United States Patent

Manoury et al.

[11] Patent Number: 4,983,607
[45] Date of Patent: Jan. 8, 1991

[54] QUINOLINONE DERIVATIVES AND THEIR PREPARATION IN THERAPY

[75] Inventors: Philippe Manoury, Verrieres Le Buisson; Daniel Obitz, Antony; Michel Peynot, L'Hay Les Roses; Jonathan Frost, Wissous, all of France

[73] Assignee: Synthelabo, Paris, France
[21] Appl. No.: 417,970
[22] Filed: Oct. 10, 1989

[30] Foreign Application Priority Data

Oct. 11, 1988 [FR] France ............... 88 13324

[51] Int. Cl.$^5$ .............. A61K 31/495; C07D 401/06; C07D 401/14
[52] U.S. Cl. ............................... 514/253; 514/254; 544/363; 546/158
[58] Field of Search ............. 544/363; 514/253, 254

[56] References Cited

U.S. PATENT DOCUMENTS 4,237,135 12/1980 Uno et al. ........................ 544/363
4,284,768 8/1981 Santilli ............................ 544/363

FOREIGN PATENT DOCUMENTS 2017701 10/1979 United Kingdom .
2071094 9/1981 United Kingdom .

Primary Examiner—Glennon H. Hollrah
Assistant Examiner—James H. Turnipseed
Attorney, Agent, or Firm—Wegner, Cantor, Mueller & Player

[57] ABSTRACT

A quinolinone derivative which is a compound of formula (I):

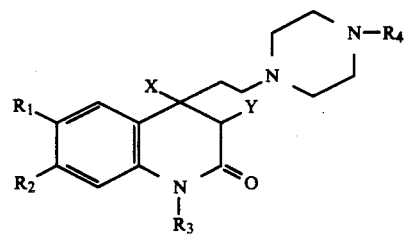

in which:
$R_1$ and $R_2$ are each, independently of one another, a hydrogen or halogen atom or a ($C_{1-4}$)alkyl radical;
$R_3$ is a hydrogen atom or a ($C_{1-4}$)alkyl radical;
$R_4$ is an unsubstituted or substituted naphthyl, tetrahydronaphthyl, benzyl, phenyl, pyridyl, isoquinolyl or benzoyl radical; and X and Y are each a hydrogen atom or together form a bond; or a pharmaceutically acceptable acid addition salt thereof and, when X and Y are each a hydrogen atom, the diastereoisomers and enantiomers thereof.

8 Claims, No Drawings

QUINOLINONE DERIVATIVES AND THEIR PREPARATION IN THERAPY

The present invention relates to quinolinone derivatives, to their preparation and to their application in therapy.

The present invention provides a quinoline derivative which is a compound of formula (I):

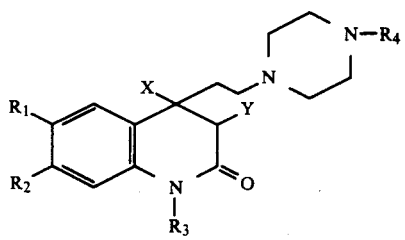

in which:

$R_1$ and $R_2$ are each, independently of one another, a hydrogen or halogen atom or a $(C_{1-4})$alkyl radical;

$R_3$ is a hydrogen atom or a $(C_{1-4})$alkyl radical;

$R_4$ is an unsubstituted or substituted naphthyl, tetrahydronaphthyl, benzyl, phenyl, pyridyl, isoquinolyl or benzoyl radical; and X and Y are each a hydrogen atom or together form a bond; or a pharmaceutically acceptable acid addition salt thereof and, when X and Y are each a hydrogen atom, the diastereoisomers and enantiomers thereof.

Examples of substituents for $R_4$ are methoxy and $(C_{3-5})$ cycloalkyl radicals and chlorine and fluorine atoms.

Preferred derivatives of the invention are those in which:

$R_1$ and $R_2$ are each, independently of one another, a hydrogen or fluorine atom or a methyl radical;

$R_3$ is a hydrogen atom or a methyl or ethyl radical; and $R_4$ is an unsubstituted or substituted naphthyl or tetrahydronaphthyl radical.

The preferred derivatives are $(\pm)$-4-{2-[4-(7 methoxy-1-naphthyl)-1-piperazinyl]ethyl}-3,4-dihydro-2(1-H)-quinolinone, or a pharmaceutically acceptable acid addition salt thereof or an enantiomer thereof, $(\pm)$-4-{2-[4-(7-methoxy-1-naphthyl)-1-piperazinyl]ethyl}-6-methyl-3,4-dihydro-2-(1H)-quinolinone, or a pharmaceutically acceptable acid addition salt thereof or an enantiomer thereof or 4-{2-[4-(1-naphthyl)-1-piperazinyl]ethyl)-2(1H)-quinolinone or a pharmaceutically acceptable acid addition salt thereof.

The derivative of the present invention may be prepared according to the reaction schemes given in Appendices 1, 2 and 3.

When X and Y together denote a bond, the derivatives may be prepared according to the reaction scheme given in Appendix I: a phenylamine (II) is reacted with 4-acetyloxy-2H,3H-pyran-2,6-dione, and the compound obtained (III) is cyclized to an acid (IV) which is converted to an ester (V) and then to an alcohol (VI) and finally to a chloride (VII) which is condensed with a 1-$R_4$-piperazine to obtain the compound (I), which is alkylated, if desired, with a compound of formula $R_3X$ in which X is a labile group.

When X and Y are each a hydrogen atom, the derivatives (I) may be prepared by hydrogenation of the oxoquinolyl ring-system at any stage of the synthesis, even at the final product stage.

The reaction scheme of Appendix 2 consists in hydrogenating the ester (V) to an ester (VIII) which is reduced to an alcohol (IX) (the latter may also be obtained by hydrogenation of the alcohol (VI)). This compound (IX) is converted to a chlorinated compound (X) which is condensed with a 1-$R_4$-piperazine to obtain the compounds (I) in which $R_3$=H, and which can optionally be alkylated with a compound of formula $R_3X$.

The enantiomers of the derivatives in which X and Y are each a hydrogen atom may be prepared according to the reaction scheme given in Appendix 3, by resolution of the acid (XI) (obtained by saponification of the ester (VIII)) according to the conventional procedure for separation of the diastereoisomeric salts resulting from the salification of this acid with optically active amines such as L-tyrosine hydrazide or 1-(1-naphthyl)ethylamine. The dextrorotatory or laevorotatory acids (XI) are then reduced via their mixed anhydrides to alcohols (IX) (of the same sign), which are then converted to dextrorotatory and laevorotatory chlorinated compounds (X). The latter are condensed with a 1-$R_4$-piperazine so as to obtain the dextrorotatory and laevorotatory compounds (I) in which $R_3$ is H, and which can optionally be alkylated.

In each case the compound of formula (I) may be formed into a pharmaceutically acceptable acid addition salt thereof, for example a maleate, fumarate, oxalate or sesquifumarate salt.

The Examples which follow illustrate the invention; the analyses and IR and NMR spectra confirm the structure of the compounds.

EXAMPLE 1

6-Methyl-4-{2-[4-(1-naphthyl)-1-piperazinyl]ethyl}-2(1H)-quinolinone (scheme Appendix 1).

1.1. 6-Methyl-2-oxo-1,2-dihydro-4-quinolineacetic acid.

(a) 50 g (0.29 mol) of 4-acetyloxy-2H,3H-pyran-2,6-dione (prepared according to E. G. Frandsen and N. Jacobsen J. Chem. Soc. Perkin, I 933–6 (1978)) are added fairly rapidly with stirring to a solution of 31 g (0.29 mol) of 4-methylaniline in 100 ml of acetic acid.

After 30 minutes' stirring at room temperature, 800 ml of water are added and the mixture is left stirring for 1 h. The solid is then drained, washed with water and dried at 50° C. for 24 h. 68.4 g (85%) of a solid, melting point 141°–142° C., are obtained.

(b) 90 g (0.325 mol) of the above anilide are added in small portions to 500 ml of sulphuric acid (95–97%), and the mixture is then heated to 100° while stirring for 2 h. After being cooled, the reaction medium is poured into 500 g of ice and 200 ml of water, the mixture is stirred and the solid is drained and washed three times with water before being dried for 8 h at 60°. 60 g (85%) of a solid, melting point 253°–255° C., are collected.

1.2. Methyl 6-methyl-2-oxo-1,2-dihydro-4-quinolineacetate 95 g (0.8 mol) of thionyl chloride are added dropwise in the course of approximately 1 h to a stirred suspension of 60 g (0.276 mol) of the above acid in 1 liter of methanol, and the mixture is left stirring for 4 h. After concentration to 500 ml and cooling in ice, the solid is drained, washed with methanol and then with ether and dried at 60° for 8 h.

57 g (89%) of a solid, melting point 219°–20° C., are obtained.

1.3. 4-(2-Hydroxyethyl)-6-methyl-2(1H)-quinolinone 56.5 g (0.244 mol) of the above ester are added portion-wise under argon to a suspension of 45.6 g (1.2 mol) of lithium aluminium hydride in 1.5 l of dry tetrahydrofuran, cooling with ice in order to maintain the temperature of the medium below 30°. After the addition, the mixture is left stirring for 4 h at room temperature. The reaction medium is hydrolysed by adding 200 ml of water very slowly, and the medium is left standing overnight and then poured into a mixture of 1 kg of ice and 200 ml of sulphuric acid; the THF is then removed by evaporation under reduced pressure. The suspension of the expected compound in acidified water is drained and the solid is washed with water and then dried. It is then washed in suspension in 500 ml of refluxing ethanol for 1 h. After the mixture is cooled, 35.5 g (72%) of a solid, melting point 252°–255° C., are drained, washed with ether and dried at 60°.

1.4. 4-(2-Chloroethyl)-6-methyl-2(1H)-quinolinone 29 ml (0.4 mol) of thionyl chloride and 10 drops of pyridine are added with stirring to a suspension of 15 g (0.074 mol) of the above carbinol in 700 ml of chloroform. An oil appears, which gradually crystallizes at room temperature. The suspension is heated to reflux of the solvent until solubilization is complete (approximately 4 h). While cooling and stirring, 400 ml of water are added slowly and cautiously to the reaction medium and the mixture is left stirring for a further 30 minutes. The crystallized product obtained is drained and the chloroform phase of the filtrate is separated after settling has taken place, washed with water and dried. After evaporation of the solvent, the residue is ground in alcohol and a second crop of solid is obtained. The two solid fractions are combined and recrystallized in ethanol. 10.25 g (62.5%) of a solid, melting point 215°–216° C., are obtained.

1.5. 6-Methyl-4-{2-[4-(1-naphthyl)-1-piperazinyl]ethyl}-2(1H)-quinolinone

A solution of 1.5 g (0.0068 mol) of the above chlorinated derivative and 3.2 g (0.015 mol) of 1-(1-naphthyl)-piperazine (described by Prelog and Blazek, Collect. Czech. Chem. Comm. 6, 211–215 (1934)) in 50 ml of alcohol is heated for 30 minutes to reflux, and the alcohol is then evaporated off to dryness. The pasty residue is heated for 1 h to 120°–130°. The resulting mixture of salt and base is an oil which is ground in saturated aqueous sodium carbonate solution, from which the water is then evaporated off to dryness. On account of their insolubility in the usual solvents, the organic bases are extracted with a methylene chloride/methanol (50:50) mixture, the resulting suspension is filtered and the filtrate concentrated. The residual oil is purified on a silica column, eluting with a methylene chloride/methanol (95:5) mixture. The fraction obtained is recrystallized from methyl Cellosolve and the isolated solid is dried at 100° under reduced pressure. 1.9 g (71%) of a solid, melting point 241°–242° C., are obtained.

EXAMPLE 2

7-Fluoro-4-{2-[4-(7-methoxy-1-naphthyl)-1-piperazinyl]ethyl}-2(1H)-quinolinone 2.1. 7-Fluoro-2-oxo-1,2-dihydro-4-quinolineacetic acid The compound is prepared according to the technique described in 1.1. from 3-fluoroaniline. It contains 17% of 5-fluoro-2-oxo-1,2-dihydro-4-quinolineacetic acid. This mixture melts at 224°–225° C.

2.2. Methyl 7-fluoro-2-oxo-1,2-dihydro-4-quinolineacetate

The compound is obtained according to the technique described in 1.2. It is 92% pure and contains 8% of methyl 5-fluoro-2-oxo-1,2-dihydro-4-quinolineacetate. It melts at 255°–256° C.

2.3. 7-Fluoro-4-(2-hydroxyethyl)-2(1H)-quinolinone

Prepared in a 70.4% yield according to the procedure described in 1.3, this product is 97.5% pure and melts at 221°–222° C.

2.4. 4-(2-Chloroethyl)-7-fluoro-2(1H)-quinolinone

Obtained according to the technique described in 1.4. in a 34% yield, this product melts at 190°–191° C.

2.5. 7-Fluoro-4-{2-[4-(7-methoxy-1-naphthyl)-1-piperazinyl]ethyl}-2(1H)-quinolinone Prepared (57%) from 1-(7-methoxy-1-naphthyl)piperazine described in French Pat. No 88/10,481 according to the technique described in 1.5. This compound melts at 250°–252° C.

EXAMPLE 3

(±)-4-{2-[4-(7-Methoxy-1-naphthyl)-1-piperazinyl]ethyl}-3,4-dihydro-2(1H)-quinolinone (scheme Appendix 2)

3.1. 3-Acetyloxy-5-oxo-5-phenylamino-2-pentenoic acid 65.7 g (0.705 mol) of aniline are added to a stirred suspension of 120 g (0.705 mol) of 4-acetyloxy-2H,3H-pyran-2,6-dione in 250 ml of acetic acid. The reaction medium is stirred for 1 h at room temperature and is then diluted by adding 500 ml of water. The solid is drained, washed with water and dried in an oven (50° C.) for 24 h. 150 g (81%) of the expected compound, melting point 125°–126° C., are obtained.

This compound is described by E. G. Frandsen and N. Jacobsen (reference cited in 1.1.).

3.2. 2-Oxo-1,2-dihydro-4-quinolineacetic acid 150 g (0.57 mol) of 3-acetyloxy-5-oxo-5-phenylamino-2-pentenoic acid are poured in small portions while stirring into 500 ml of 95–97% sulphuric acid, and the reaction medium is then heated to 100° C. for 2 h. After being cooled, this solution is poured into a mixture of 1 kg of ice and 500 ml of water while stirring. The solid thereby obtained is drained. It is washed with 3 times 100 ml of water and dried for 8 h at 60° C. 60.5 g (52%) of 2-oxo-1,2-dihydro-4-quinolineacetic acid, melting point 213°–215° C., are obtained.

This compound is described by E. Besthorn and E. Garben, Chem Ber. (1900), 33, 3439.

3.3. Methyl 2-oxo-1,2-dihydro-4-quinolineacetate 95 g (0.8 mol) of thionyl chloride are added dropwise in the course of approximately 1 h to a stirred suspension of 60 g (0.295 mol) of 2-oxo-1,2-dihydro-4-quinolineacetic acid in 1 l of methanol. The mixture is left overnight. The solvent is driven off and the residue obtained is dissolved in 300 ml of boiling methanol. After the mixture is cooled, 300 ml of ether are added. The solid is drained and then recrystallized in methanol. 51.5 g (80%) of methyl 2-oxo-1,2-dihydro-4-quinolineacetate, melting point 209°–210° C., are obtained This product is described by M. Uchida, F. Tabusa, M. Komatsu, S. Morita, T. Kanbe and K. Nakagawa Chem. Pharm. Bull. (1985), 33, 3775. 3.4. Methyl (±)-2-oxo-1,2,3,4-tetrahydro-4-quinolineacetate.

50 g (0.23 mol) of methyl 2-oxo-1,2-dihydro-4-quinolinacetate dissolved in 1 l of methanol is subjected to hydrogenation in a Parr apparatus in the presence of 2 g of Adams' platinum oxide under 40 to 45 psi and at 60° C. for approximately 1 h. After the catalyst is filtered off and the solvent evaporated off, the oily residue is chromatographed on silica. Elution with a dichloromethane/acetone (95:5) mixture yields an oil, which is solubilized in 250 ml of boiling toluene. After being cooled, this solution is diluted with 250 ml of petroleum ether. The crystalline product thereby obtained is drained, washed and dried. 36.8 g (73%) of methyl (±)-2-oxo-1,2,3,4-tetrahydro-4-quinolineacetate, melting point 115°-116° C., are obtained.

3.5. (±)-4-(2-Hydroxyethyl)-3,4-dihydro-2(1H)-quinolinone

A solution of 11 g (0.05 mol) of methyl (±)-2-oxo-1,2,3,4-tetrahydro-4-quinolineacetate in 50 ml of dioxane is poured dropwise while stirring under an inert atmosphere into a suspension of 2.65 g (0.07 mol) of lithium aluminium hydride in 250 ml of dry ether. The mixture is then heated for 4 h to reflux. After cooling, the reaction is hydrolysed by the slow addition of 10 ml of water with vigorous stirring. The suspension is filtered and the inorganic solid is washed with 20 ml of dioxane. The filtrate is evaporated and the oil obtained is ground in ether, causing it to crystallize. The solid is recrystallized in ethyl acetate. 5.3 g (55%) of (±)-4-(2-hydroxyethyl)-3,4-dihydro-2(1H)-quinolinone, melting point 119°-120° C., are obtained.

3.6. (±)-4-(2-Chloroethyl)-3,4-dihydro-2(1H)-quinolinone

A mixture of 5.2 g (0.027 mol) of (±)-4-(2-hydroxyethyl)-3,4-dihydro-2(1H)-quinolinone, 15 g (0.126 mol) of thionyl chloride, 200 ml of dry chloroform and 10 drops of pyridine is heated to reflux for 4 h. After the mixture is cooled, 50 ml of water are added dropwise and the mixture is stirred for 30 minutes. The organic phase is separated after settling has taken place, dried over magnesium sulphate and concentrated under vacuum. The residue is chromatographed on a silica column. Elution with a dichloromethane/acetone (90:10) mixture yields an oil which is crystallized in cyclohexane. 5 g (88%) of (±)-4-(2-chloroethyl)-3,4-dihydro-2(1H)-quinolinone, melting point 112°-113° C., are obtained.

3.7 (±)-4-{2-[4-(7-Methoxy-1-naphthyl)-1-piperazinyl]ethyl}-3,4-dihydro-2(1H)-quinolinone 1.5 g (7.15 mmol) of (±)-4-(2-chloroethyl)-3,4-dihydro-2(1H)-quinolinone are mixed intimately with 3.65 g (15 mmol) of 1-(7-methoxy-1-naphthyl)piperazine and the mixture is heated to 130° C. for 1 h while stirring. The cooled residue is taken up between 25 ml of 2N sodium hydroxide and twice 50 ml of dichloromethane. The organic extract is washed with water, dried over magnesium sulphate and concentrated. The residue is purified by elution with a dichloromethane/methanol (95:5) mixture on a silica column. The purified fraction is crystallized in ether and this solid is drained and dried. 2.6 g (87.5%) of (±)-4-{2-[4-(7-methoxy-1-naphthyl)-1-piperazinyl]ethyl}-3,4-dihydro-2(1H)-quinolinone, melting point 177°-178° C., are obtained.

3.8. (±)-4-{2-[4-(7-Methoxy-1-naphthyl)-1-piperazinyl]ethyl}-3,4-dihydro-2(1H)-quinolinone sesquifumarate (base/acid 2:3)

1.06 g (9.1 mmol) of fumaric acid are added to a solution of 2.5 g (6.02 mmol) of the above base in 100 ml of boiling ethanol. When solubilization is complete in the heated state, the solution is allowed to cool slowly. The crystallized salt is drained, washed with alcohol and then dried under reduced pressure at 100° C. 2.9 g (82%) of (±)-4-{2-[4-(7-methoxy-1-naphthyl)-1-piperazinyl]ethyl}-3,4-dihydro-2(1H)-quinolinone sesquifumarate (base/acid 2:3), melting point 208°-209° C., are obtained.

The preparation process of Appendix 2 may be used for obtaining the compound 3.5

4-(2-Hydroxyethyl)-2(1H)-quinolinone is prepared from methyl 2-oxo-1,2-dihydro-4-quinolineacetate (prepared in 3.3.) according to the procedure described in 1.3. It is a solid, melting point 213°-5° C. A catalytic hydrogenation of this compound is performed with Adams+ platinum to obtain (±)-4-(2-hydroxyethyl)-3,4-dihydro-2(1H)-quinolinone.

EXAMPLE 4

4-{2-[4-(1-Naphthyl)-1-piperazinyl]ethyl}-1-methyl-2-quinolinone.

4.1. 4-(2-Chloroethyl)-2(1H)-quinolinone

This compound is prepared from the carbinol described in 3.9. according to the technique described in 1.4. 62.5% of a solid, melting point 212°, are obtained. This compound is described in German Offenlegungsschrift No. 3,324,034 (5/1/84) of Otsuka Pharm. Co. Ltd., with a melting point of 186°-187° C.

4.2. 4-{2-[4-(1-Naphthyl)-1-piperazinyl]ethyl}-2(1H)-quinolinone

This compound is obtained in a 50% yield by following the technique described in 1.5., and melts at 230°-232° C.

4.3. 4-{2-[4-(1-Naphthyl-)-1-piperazinyl]ethyl}-1-methyl-2-quinolinone

A suspension of 0.312 g of sodium hydride (washed with pentane) in 50 ml of dimethyl sulphoxide is heated for 1 h to 60°-70° under argon. To this solution, cooled, 2.5 g (6.5 mmol) of the above compound are added at room temperature, the mixture is left stirring for 30 minutes and then cooled to 10° and a solution of 1 g of methyl iodide in 10 ml of DMSO is added. After 12 h of reaction at room temperature, 200 ml of water are added, and a gummy solid is drained and is eluted on a silica column with a methylene chloride/methanol (95:5) mixture. Since the purified fraction melts at too low a temperature, its monofumarate is prepared in ethanol. After crystallization, draining and washing with ether, 2.2 g (66%) of a solid, melting point 208°-209° C., are obtained.

EXAMPLE 5

(+)-4-{2-[4-(7-Methoxy-1-naphthyl)-1-piperazinyl]ethyl}-3,4-dihydro-2(1H)-quinolinone.

5.1. (±)-2-Oxo-1,2,3,4-tetrahydro-4-quinolineacetic acid.

11 g of 97% pure NaOH (0.27 mol) are added with stirring to a suspension of 58 g (0.265 mol) of the ester obtained in 3.4. in 500 ml of a methanol/water (50:50) solution. After 1 h of stirring at room temperature, the homogeneous solution is left standing overnight. After evaporation of the methanol, 250 ml of water are added, followed by 6N HCl, added dropwise with stirring, to pH 1.

The precipitated acid is filtered off after 1 h of stirring at room temperature. It is washed 3 times with water and dried at 100° C. under vacuum. 52.5 g (96.5%) of a solid, melting point 183°-184° C., are obtained.

5.2. L-Tyrosine hydrazide salt of (+)-2-oxo-1,2,3,4-tetrahydro-4-quinolineacetic acid 20.5 g (0.1 mol) of the acid obtained in 5.1. are added to a boiling solution of 19.5 g (0.1 mol) of L-tyrosine hydrazide in 1 l of methanol/water (90:10).

The reaction mixture is stirred for 4 h while being maintained at 30°–40° C., and is then left standing overnight at room temperature. The solid is filtered off, washed with methanol and dried. After 2 recrystallizations in a $CH_3OH/H_2O$ (90:10) mixture, 8.25 g (20.6%) of a compound, melting point 209°–210° C., are obtained.

$[\alpha]_D^{24} = +32.5°$ (c=1, DMF)

5.3. (+)-2-Oxo-1,2,3,4-tetrahydro-4-quinolineacetic acid

A suspension of 8 g of L-tyrosine hydrazide salt obtained in 5.2. in 250 ml of distilled water is heated to dissolution. 5 ml of concentrated (36–38%) hydrochloric acid are added with stirring and the dextrorotatory acid is allowed to crystallize in the cold (5°–10° C. approximately).

The product is filtered off, washed 3 times with a minimum amount of ice-cold water and dried for 8 h at 100° C. under vacuum. 3.8 g (93%) of a solid, melting point 154°–155° C., are obtained.

$[\alpha]_D^{20} = +63.2°$ (c=1, DMF).

5.4. (+)-4-(2-Hydroxyethyl)-3,4-dihydro-2(1H)-quinolinone

A solution of 4.1 g (0.02 mol) of the acid obtained in 5.3. and 2.02 g (0.2 mol) of triethylamine in 100 ml of anhydrous THF is cooled to −10° C. with stirring and in a dry argon atmosphere.

A solution of 2.17 g (0.02 mol) of ethyl chloroformate in 10 ml of dry THF is added dropwise in the course of 15 min. After 1 h of stirring at −5° C. to −7° C., 1.5 g (0.04 mol) of sodium borohydride are added portionwise in the course of approximately 5 min. The mixture is allowed to return to room temperature and is stirred for a further 30 min. 20 ml of water are added dropwise (in the course of approximately 30 min). The organic phase is separated after settling has taken place, and the residual aqueous phase containing insoluble inorganic matter is extracted 3 times with dichloromethane. The extracts are dried over magnesium sulphate, the solvent is evaporated off and the product is purified on a silica column with the eluent dichloromethane/methanol (95:5).

The purified fraction is evaporated. 2.7 g (70.7%) of an oil are obtained, and this crystallizes on grinding in ether. Melting point: 105°–106° C.

$[\alpha]_D^{20} = +44.5°$ C. (c=1, DMF)

5.5. (+)-4-(2-Chloroethyl)-3,4-dihydro-2(1H)-quinolinone 2.5 g (13.07 mmol) of the compound of 5.4., 5 ml (69 mmol) of thionyl chloride, 5 drops of pyridine and 100 ml of dry chloroform are heated for 4 h to the refluxing temperature under dry nitrogen. In the cold state, 30 ml of water are added dropwise and with stirring, and the phases are separated after settling has taken place.

The chloroform extract, dried over magnesium sulphate and evaporated, is then purified on a silica column with the eluents dichloromethane/acetone (95:5, then 90:10).

The purified fractions give an oil which crystallizes on grinding in cyclohexane. After filtration, washing with pentane and drying for 8 h at 60° C. under vacuum, 1.3 g (47.5%) of a compound, melting point 110°–111° C., are obtained.

$[\alpha]_D^{20} = +77.1°$ (c=1, DMF).

5.6. (+)-4-{2-[4-(7-Methoxy-1-naphthyl)-1-piperazinyl]ethyl}-3,4-dihydro-2(1H)-quinolinone.

1.2 g (5.72 mmol) of derivative of 5.5., 1.45 g (6 mmol) of 1-(7-methoxy-1-naphthyl)piperazine, 20 ml of methyl isobutyl ketone (MIBK) and a few crystals of sodium iodide are heated for 4 h to the refluxing temperature. 0.32 g (3 mmol) of sodium carbonate is added and the mixture is heated to the refluxing temperature for 8 h.

0.32 g (3 mmol) of sodium carbonate is added again and the mixture is left refluxing for a further 8 h. After the addition of 1 ml of water and 4 h of refluxing, the MIBK is evaporated off and the residue is taken up with 50 ml of water. The base is extracted with dichloromethane. The extract, dried over magnesium sulphate and evaporated, is purified on a silica column with the eluent dichloromethane/methanol (95:5).

The purified fraction crystallizes in ether and the solid is recrystallized in isopropyl alcohol. 1.55 g (65%) of a solid, melting point 149°–150° C., are obtained.

$[\alpha]_D^{25} = +50.5°$ (c=1, DMF).

EXAMPLE 6

(−)-4-{2-[4-(7-Methoxy-1-naphthyl)-1-piperazinyl]ethyl}-3,4-dihydro-2(1H)-quinolinone 6.1. (+)-1-(1-Naphthyl)ethylamine salt of (−)-2-oxo-1,2,3,4-tetrahydro-4-quinolineacetic acid The mother liquors from the 3 recrystallizations of the L-tyrosine hydrazide salt of (±)-2-oxo-1,2,3,4-tetrahydro-4-quinolineacetic acid (see Example 5.2.) are evaporated to dryness. The residue is dissolved in 200 ml of water at 50°–60° C. and 20 ml of concentrated hydrochloric acid are added.

The acid enriched in the laevorotatory enantiomer crystallizes in the cold and melts at 178°–180° C.

13.5 g (65.8 mmol) of this enriched acid and 11.3 g (66 mmol) of (R)-(+)-1-(1-naphthyl)ethylamine are dissolved in 350 ml of boiling isopropyl alcohol.

The reaction mixture is filtered at room temperature after 4 h of stirring and the solid is washed with ether.

After 2 recrystallizations in an isopropyl alcohol/water (95:5) mixture, 6.1 g (24.6%) of a compound, melting point 192°–193° C., are obtained.

$[\alpha]_D^{20} = -1.75°$ (c=1, DMF).

6.2. (−)-2-Oxo-1,2,3,4-tetrahydro-4-quinolineacetic acid

A suspension of 6 g (15.9 mmol) of the above salt of 6.1. in 100 ml of distilled water and 5 ml of concentrated (36–38%) hydrochloric acid is heated to dissolution.

The product is allowed to crystallize in the cold (5°–10° C. approximately). The solid is filtered off and washed with ice-cold water. It is dried for 8 h at 100° C. under vacuum, and 2.95 g (90.5%) of a compound, melting point 154°–155° C., are obtained.

$[\alpha]_D^{20} = -62.7°$ (c=1, DMF).

6.3. (−)-4-(2-Hydroxyethyl)-3,4-dihydro-2(1H)-quinolinone

A solution of 2.85 g (13.9 mmol) of (−)-2-oxo-1,2,3,4-tetrahydro-4-quinolineacetic acid and 1.42 g (14 mmol) of triethylamine in 70 ml of dry THF is cooled to −10° C. with stirring under dry argon.

A solution of 1.52 g (14 mmol) of ethyl chloroformate in 10 ml of dry THF is added dropwise in the course of 20 min. After 1 h of stirring at −5° C., 1.13 g (30 mmol) of sodium borohydride are added portionwise in the course of 5 min.

The reaction mixture is allowed to return to room temperature while being stirred for a further 30 min, and 15 ml of water are then added dropwise. The medium is evaporated and the residue is extracted with dichloromethane (3×50 ml). The extract, dried over magnesium sulphate and evaporated, is then purified on a silica column with the eluent dichloromethane/methanol (95:5). The purified fraction gives an oil on evaporation. The product crystallizes on grinding in ether. 1.9 g (71.4%) of a solid, melting point 105°–106° C., are obtained.

$[\alpha]_D^{25} = -44.7°$ (c=1, DMF).

6.4.  (−)-4-(2-Chloroethyl)-3,4-dihydro-2-(1H)-quinolinone 1.8 g (9.4 mmol) of the compound of 6.3., 3.4 ml of thionyl chloride (∼47 mmol), 70 ml of dry chloroform and 5 drops of pyridine are heated for 4 h to reflux under dry nitrogen.

In the cold state, an excess of water is added dropwise with vigorous stirring, and the phases are separated after settling has taken place. The chloroform extract is dried over magnesium sulphate, and then evaporated and purified on a silica column with the eluent dichloromethane/acetone (90:10). The purified fraction gives, after dissolution in the heated state, an oil which crystallizes in cyclohexane. 1.55 g (79%) of a solid, melting point 109°–110° C., are obtained.

$[\alpha]_D^{20} = -76.8°$ (c=1, DMF).

6.5.  (−)-4-{2-[4-(7-Methoxy-1-naphthyl)-1-piperazinyl]ethyl}-3,4-dihydro-2(1H)-quinolinone 1.45 g (6.9 mmol) of the chlorinated derivative of 6.4., 1.7 g (7 mmol) of 1-(7-methoxy-1-naphthyl)piperazine, a few crystals of sodium iodide and 20 ml of methyl isobutyl ketone are heated for 4 h to the refluxing temperature.

0.37 g (3 mmol) of sodium carbonate is added and the reaction mixture is brought to the refluxing temperature for 8 h. 0.37 g of sodium carbonate is added again and the mixture is left refluxing for a further 8 h. After the addition of 1 ml of water and 4 h of refluxing, the methyl isobutyl ketone is evaporated off and the residue is taken up with 50 ml of water. The base is extracted with dichloromethane.

The extract, dried over magnesium sulphate and evaporated, is purified on a silica column with the eluent dichloromethane/methanol (95:5). The purified fraction crystallizes in ether, and the solid is recrystallized in isopropyl alcohol. After filtration and drying, 1.8 g (68%) of crystals, melting point 149°–150° C., are obtained.

$[\alpha]_D^{25} = -49.8°$ (c=1, DMF).

TABLE

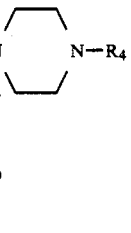

(I)

| Compound | $R_1$ | $R_2$ | $R_3$ | X,Y | $R_4$ | M.p. (°C.) (salt) |
|---|---|---|---|---|---|---|
| 1 | H | H | H | bond | 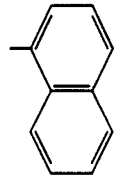 | 230–2 |
| 2 | H | F | H | bond | 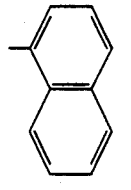 | 226–7 |
| 3 | H | H | H | bond | (ethylphenyl) | 167–8 |
| 4 | H | H | H | bond | 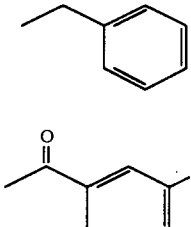 | 172–4 |

TABLE-continued
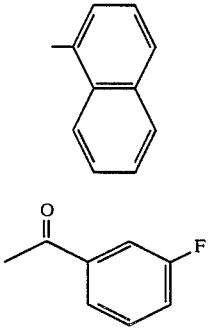
(I)
| Compound | R₁ | R₂ | R₃ | X,Y | R₄ | M.p. (°C.) (salt) |
|---|---|---|---|---|---|---|
| 5 | CH₃ | H | H | bond | 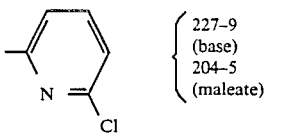 | 241-2 |
| 6 | CH₃ | H | H | bond | 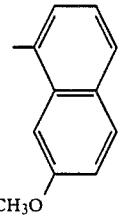 | 254-6 |
| 7 | CH₃ | H | H | bond | 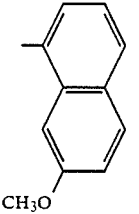 | 227-9 (base) 204-5 (maleate) |
| 8 | H | H | H | bond | 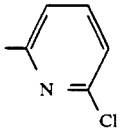 | 234-5 |
| 9 | H | F | H | bond | 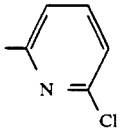 | 250-2 |
| 10 | H | H | H | bond | 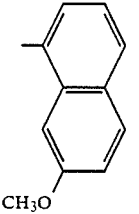 | 236-8 (base) 206-6 (maleate) |
| 11 | H | H | H | H,H | 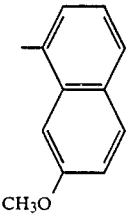 | 177-8 (base) 208-9 (sesqui fumarate) |

TABLE-continued
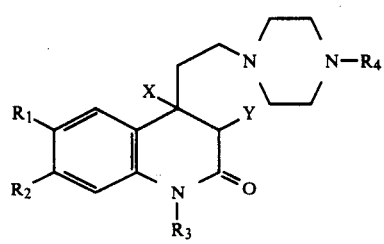
(I)
| Compound | $R_1$ | $R_2$ | $R_3$ | X,Y | $R_4$ | M.p. (°C.) (salt) |
|---|---|---|---|---|---|---|
| 12 | H | H | $CH_3$ | bond | 1-naphthyl | 208–9 (fumarate) |
| 13 | H | H | $CH_2CH_3$ | bond | 1-naphthyl | 197–8 (fumarate) |
| 14 | H | H | H | bond | isoquinolin-1-yl | 226–7 |
| 15 | H | H | H | bond | 3-chlorophenyl | 215–6 |
| 16 | $CH_3$ | H | H | H,H | 7-methoxynaphth-1-yl | 181–2 (base) 226–7 (fumarate) |
| 17 | H | H | H | bond | 6-methoxy-1,2,3,4-tetrahydronaphth-1-yl | 180–1 |

TABLE-continued
(I)
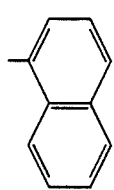
| Compound | R₁ | R₂ | R₃ | X,Y | R₄ | M.p. (°C.) (salt) |
|---|---|---|---|---|---|---|
| 18 | H | H | H | H,H | 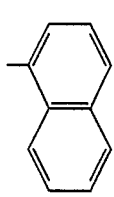 | 175-6 (base)<br>237-8<br>(fumarate) |
| 19 | CH₃ | H | H | H,H | 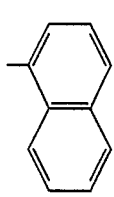 | 181-2 (base)<br>203-5<br>(fumarate) |
| 20 | H | H | H | H,H | 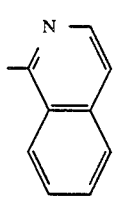 | 167-8 (base)<br>209-10<br>(fumarate) |
| 21 | CH₃ | H | H | H,H | 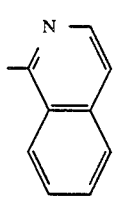 | 168-9 (base)<br>200-2<br>(fumarate) |
| 22 | H | H | CH₃ | H,H | 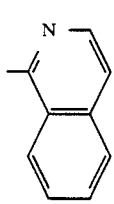 | 135-6 (base)<br>192-3<br>(fumarate) |
| 23 | H | H | H | H,H | 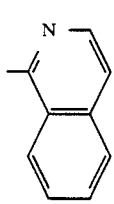 | 101-2 (base)<br>228-9<br>(fumarate) |

TABLE-continued
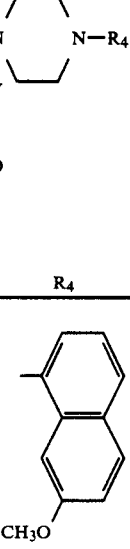
(I)
| Compound | R₁ | R₂ | R₃ | X,Y | R₄ | M.p. (°C.) (salt) |
|---|---|---|---|---|---|---|
| 24 | H | H | CH₃ | H,H | 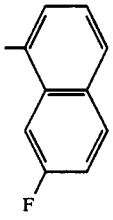 | 226-7 (oxalate) |
| 25 | H | H | H | bond | 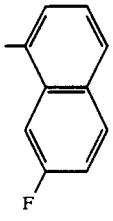 | 225-6 |
| 26 | H | H | H | H,H | 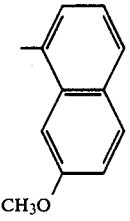 | 197-8 (base) 225-6 (fumarate) |
| 27 (+) | H | H | H | H,H | 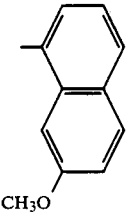 | 149-50 |
| 28 (−) | H | H | H | H,H | 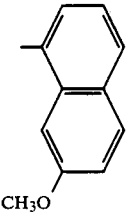 | 149-50 |

TABLE-continued

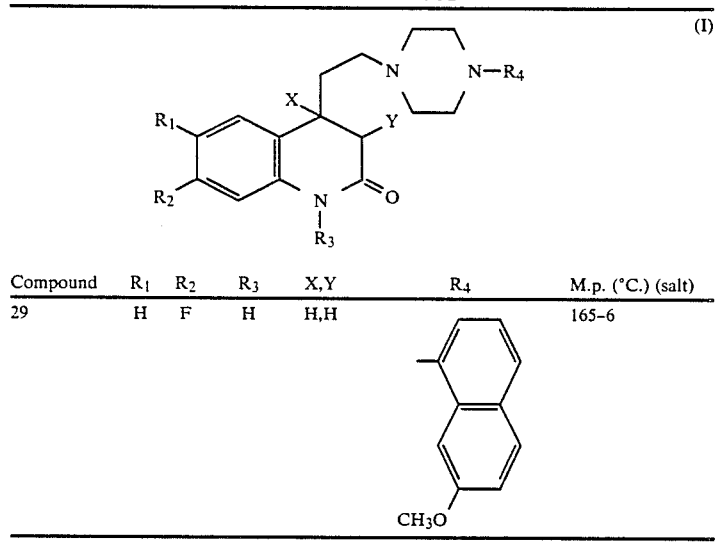

| Compound | R₁ | R₂ | R₃ | X,Y | R₄ | M.p. (°C.) (salt) |
|----------|----|----|----|-----|-----|-------------------|
| 29 | H | F | H | H,H | (7-methoxynaphth-1-yl) | 165-6 |

The compounds of the invention were subjected to a series of pharmacological tests which demonstrated their value as substances having therapeutic activity.

Thus, they were subjected to a study in respect of their affinity for 5-HT$_{1A}$ type serotoninergic receptors. In the rat hippocampus, the compounds displace a labelled specific ligand, [$^3$H]-8-hydroxy-2-dipropylaminotetralin (hereinafter designated "[$^3$H]-8-OH-DPAT"), described by Gozlan et al., Nature, (1983), 305, 140–142.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed three times at 4° C. by centrifuging them on each occasion at 48,000×g and resuspending the pellet for 10 min in cooled fresh buffer. Finally, the last pellet is suspended in the buffer to produce a concentration of 100 mg of original tissue per ml of 50 mM buffer. The suspension is then left to incubate at 37° C. for 10 min.

The binding with [$^3$H]-8-OH-DPAT is determined by incubating 10 μl of membrane suspension in a final volume of 1 ml of buffer containing 10 μM pargyline.

After incubation, the membranes are recovered by filtration on Whatman GF/B filters, which are washed three times with 5-ml aliquot portions of ice-cold buffer. The filters are extracted in scintillation fluid and their radioactivity is measured by liquid scintigraphy. The specific binding of [$^3$H]-8-OH-DPAT is defined as the quantity of radioactivity retained on the filters and capable of being inhibited by coincubation in 10 μM 5-hydroxytryptamine. At a [$^3$H]-8-OH-DPAT concentration of 1 nM, the specific binding represents from 70 to 80% of the total radioactivity recovered on the filter.

For each concentration of test compounds, the percentage inhibition of the binding with [$^3$H]-8-OH-DPAT, and then the IC$_{50}$ concentration, the concentration which inhibits 50% of the binding, are determined.

For the compounds of the invention, the IC$_{50}$ values lie between 0.001 and 0.03 μM.

The central activity of the compounds of the invention was assessed by their effects on the "PGO (pontogeniculooccipital) spikes" induced by reserpine (PGO-R test) in cats, according to the method described by H. Depoortere, Sleep 1976, 3rd Europ. Congr. Sleep Res., Montpellier 1976, 358–361 (Karger, Basel 1977).

Cumulative doses of test compounds are administered from 0.01 to 3 mg/kg intravenously) at 30-min time intervals, 4 h after the intraperitoneal injection of a dose of 0.75 mg/kg of reserpine, to curarised cats under artificial ventilation. The electroencephalographic and phasic (PGO-R spike) activities are obtained using cortical and deep (lateral geniculate) electrodes. For each dose of test compound, the percentage decrease in the number of PGO spikes, and then the AD$_{50}$, the active dose which decreases this number of spikes by 50%, are determined.

For the compounds of the invention, the intravenous AD$_{50}$ values lie between 0.001 and 0.1 mg/kg.

The results of the tests show that some of the compounds of general formula (I) possess a high affinity and a high selectivity for 5-HT$_{1A}$ type serotoninergic receptors. In vivo, they show either an agonist or a partial agonist or an antagonist activity in respect of these receptors.

Some compounds of the invention possess, in addition, an antiserotonin activity in respect of the 5HT2 type receptors.

This activity was demonstrated "in vitro" by the displacement of ligands bound specifically to serotoninergic receptors (SBS binding test), and "in vivo" by antagonism of the effects of serotonin at peripheral level (OES test) and at central level (AHT test).

SBS Test: the compounds of the invention were subjected to a test of displacement of the binding of spiroperidol to the serotoninergic (5-HT2) receptors of rat cerebral cortex.

For this test, rat brains are removed and the cortex is dissected out and homogenized at 0° C. in 10 volumes of a mixture containing, per liter, 50 millimoles of Tris/HCl buffer at pH 7.4, 120 millimoles of sodium chloride and 5 millimoles of potassium chloride. The homogeneous mixture is centrifuged at 40,000×g for 10 min, and the pellet is then recovered, washed by suspending it in the same buffer mixture, homogenized again and centrifuged, repeating this treatment of the pellet a second time. Lastly, the final pellet is diluted in the same buffer mixture on the basis of 100 mg of wet tissue per ml of buffer.

The tissue is then subjected to a prior 10-min incubation at 37° C. in the presence of 10 micromoles/l of pargyline, and then to a 20-min incubation at 37° C. in the presence of [$^3$H]spiroperidol (specific activity: 25.6 Ci per millimole) at a concentration of 0.3 nanomole/l and test compound at concentrations ranging from 0.0001 to 100 micromoles/l.

1-ml aliquots are removed and filtered under vacuum, and the filters are washed twice with 5 ml of cold buffer and dried. The radioactivity is measured in toluene in the presence of 5 g/l of 2,5-diphenyloxazole (PPO) and 0.1 g/l of 1,4-bis(5-phenyl-2-oxazolyl)benzene (POPOP).

To assess the activity of the compounds, the curve is plotted for the percentage inhibition of the specific binding of [$^3$H]spiroperidol as a function of the concentration of displacing drug. The IC$_{50}$ concentration, the concentration which inhibits 50% of the specific binding, is determined graphically.

The specific binding is defined as the binding displaced by 100 micromoles/l of 5-HT.

The IC$_{50}$ concentrations of the compounds of the invention lie for the most part between 1 and 50 nanomoles/l.

OES Test: the antiserotoninergic activity of the compounds of the invention was also demonstrated by their effect on serotonin-induced oedema in rats, according to the method described by Maling et al., J. Pharmacol. Exp. Therap., 191 (2), 300–310 (1974).

The animals are CD strain male rats (Ch. River, France) weighing 120 to 150 g, fasted for 18 h and distributed in randomized sets.

The compounds, dissolved or suspended in Tween 80 ® at a concentration of 1%, are administered orally on the basis of 0.5 ml per 100 g of bodyweight, 1 h before the sub-plantar injection of 1 µg of serotonin (dissolved in sterile physiological saline, in a volume of 0.1 ml) into one of the hind legs. The volume of the oedema is measured 1 h after the injection of serotonin by means of an Ugo Basile mercury plethysmometer. The AD$_{40}$ (dose which decreases by 40% the volume of the oedema, relative to the control animals) is determined graphically.

The AD$_{40}$ of the compounds of the invention, determined orally, is between 0.1 and 2 mg/kg.

AHT Test: the antiserotoninergic activity of the compounds was studied in respect of their effect on the antagonism of "head twitches" induced by L-5-hydroxytryptophan (L-5-HTP) in mice, according to the method described by Corne et al., Br. J. Pharmacol., 20, 106–120 (1962).

The mice (CD1 males, Charles River France; 18–22 g of bodyweight) receive the test products at increasing doses, or the solvent, intraperitoneally or orally, simultaneously with (i.p. administration) or sixty minutes before (oral administration) a subcutaneous injection of L-5-HTP at a dose of 250 mg/kg. Forty-five minutes after this injection of 5-HTP, the number of twitches is counted, for each mouse, for one minute.

For each treatment, the mean number of twitches, as well as the percentage change relative to the control batch, are calculated.

From the dose-response curve, the AD$_{50}$ (50% active dose or dose which decreases by 50% the mean number of twitches relative to the control animals) is determined by the graphic method of Miller and Tainter (Proc. Soc. Exp. Biol. Med., (1944), 57, 261).

The AD$_{50}$ values of the compounds of the invention lie between 0.05 and 2 mg/kg when administered intraperitoneally and between 1 and 4 mg/kg when administered orally.

The compounds of the invention may be used for the treatment of migraine, anxiety, depression, obesity, schizophrenia, vascular or gastrointestinal spasms, hypertension and platelet aggregation, and as antiemetics. They may also be used for the treatment of psycho-behavioural disorders of cerebral senescence.

The present invention also provides a compound of formula (I), or a pharmaceutically acceptable acid addition salt thereof, for use in a method of treatment of the human or animal body by therapy, in particular for treating migraine, anxiety, depression, obesity, schizophrenia, vascular or gastrointestinal spasms, hypertension, platelet aggregation, a psycho-behavioral disorder of cerebral senescence or for use as an antiemetic.

The compounds of the invention may be administered orally or parenterally, in combination with any suitable excipient.

The present invention further provides a pharmaceutical composition which comprises a compound of formula (I) or a pharmaceutically acceptable acid addition salt thereof and a pharmaceutically acceptable excipient.

The daily dosage can range from 1 to 1,000 mg.

APPENDIX

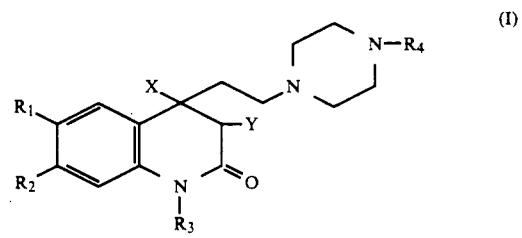

APPENDIX 1
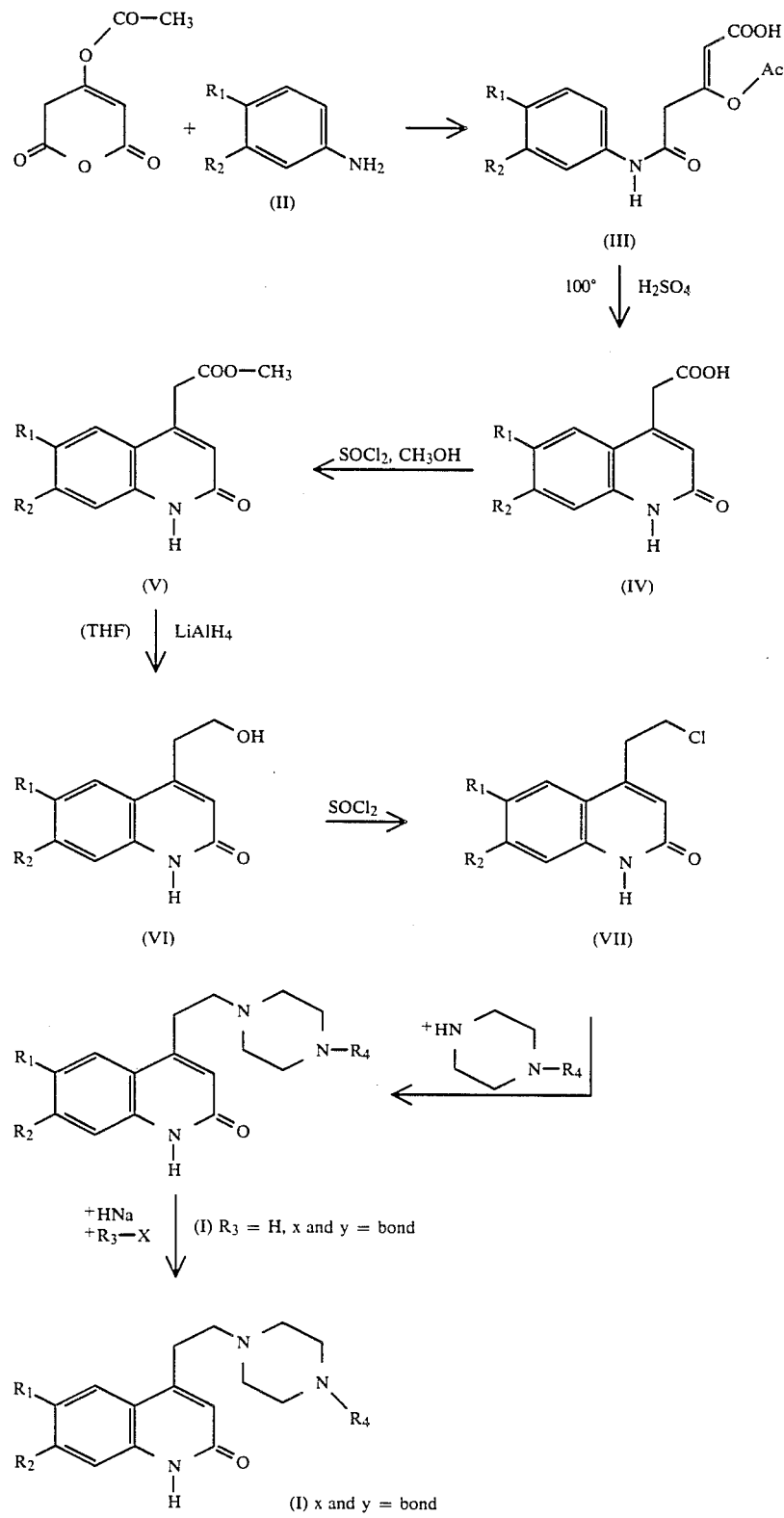

APPENDIX 2
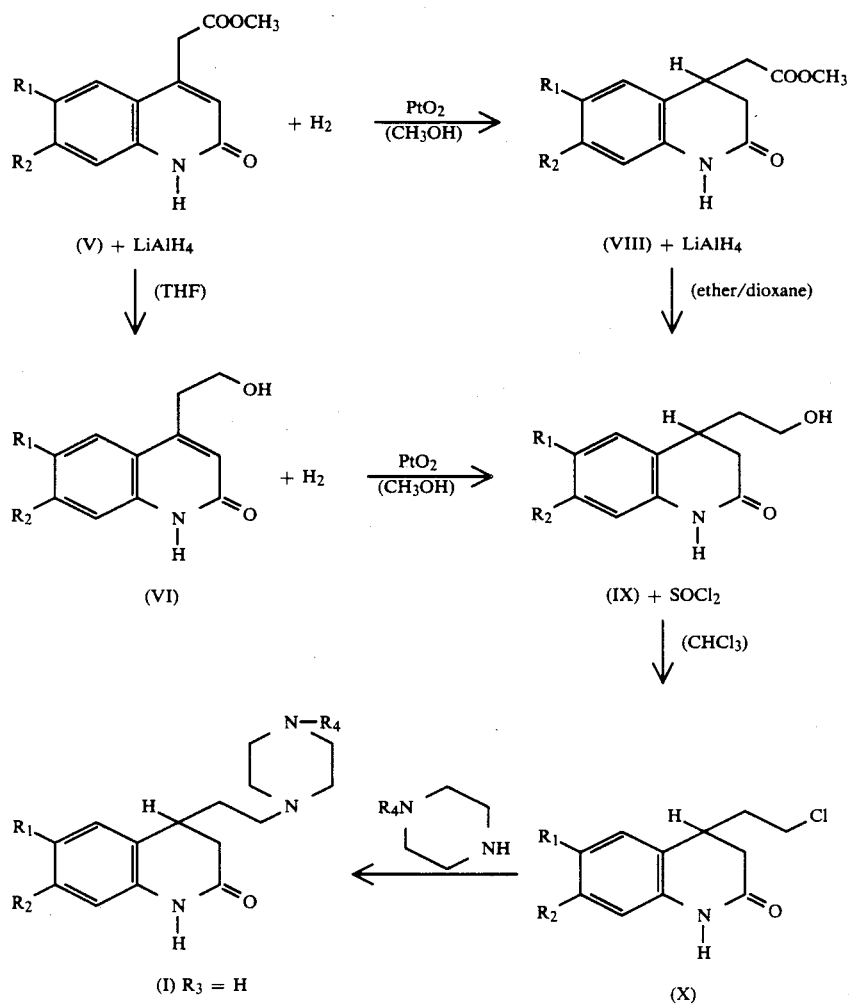
APPENDIX 3
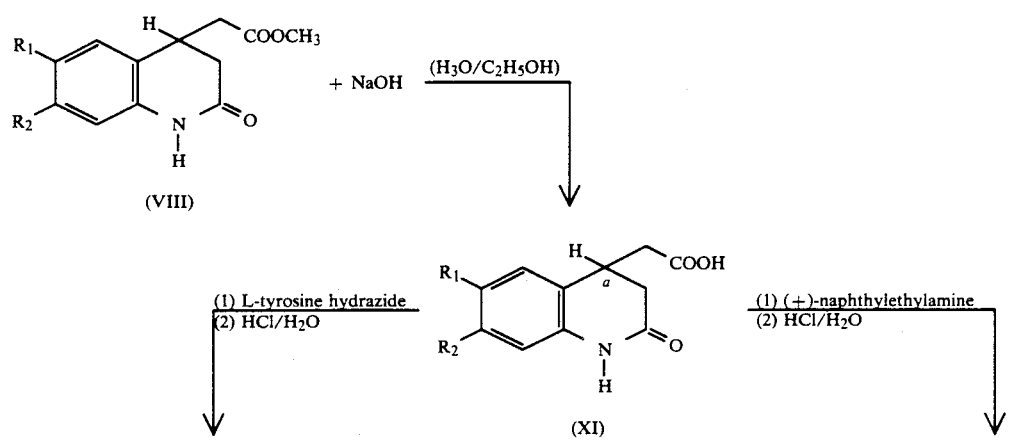

-continued
APPENDIX 3

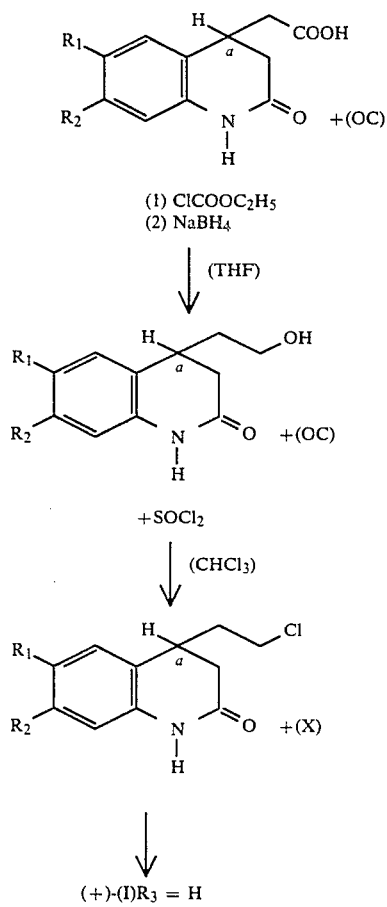

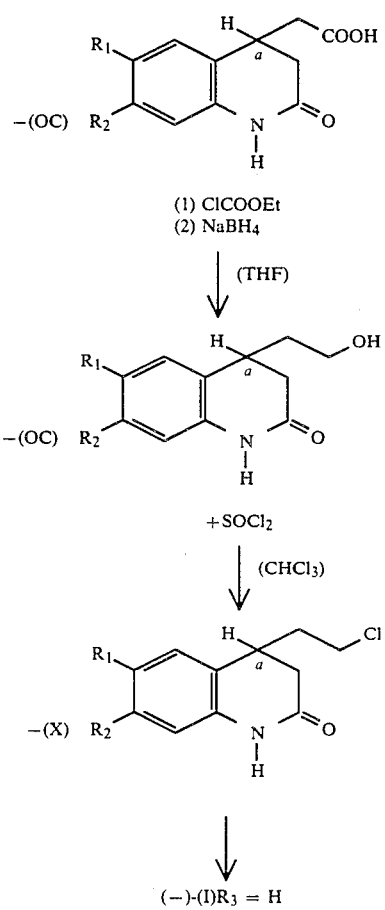

We claim:
1. A quinolinone derivative which is a compound of formula (I):

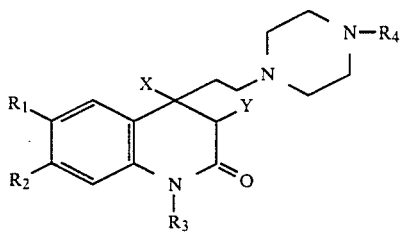

in which
R$_1$ and R$_2$ are each, independently of one another, a hydrogen or halogen atom or a (C$_{1-4}$)alkyl radical;
R$_3$ is a hydrogen atom or a (C$_{1-4}$)alkyl radical;
R$_4$ is an unsubstituted or substituted naphthyl, tetrahydronaphthyl, benzyl, phenyl, pyridyl, isoquinolyl or benzoyl radical; and
X and Y are each a hydrogen atom or together form a bond; or a pharmaceutically acceptable acid addition salt thereof and, when X and Y are each a hydrogen atom, the diastereoisomers and enantiomers thereof.

2. A derivative according to claim 1 in which R$_4$ is a naphthyl, tetrahydronaphthyl, benzyl, phenyl, pyridyl, isoquinolyl or benzoyl radical substituted by a methoxy or (C$_{3-5}$) cycloalkyl radical or by a chlorine or fluorine atom.

3. A derivative according to claim 1, in which: R$_1$ and R$_2$ are each, independently of one another, a hydrogen or fluorine atom or a methyl radical;
R$_3$ is a hydrogen atom or a methyl or ethyl radical; and
R$_4$ is an unsubstituted or substituted naphthyl or tetrahydronaphthyl radical.

4. A derivative according to claim 1, which is in the form of a maleate, fumarate, oxalate or sesquifumarate salt thereof.

5. A derivative according to claim 1, which is (±)-4-{2-[4-(7-methoxy-1-naphthyl)-1-piperazinyl]ethyl}-3,4-dihydro-2(1-H)-quinolinone, or a pharmaceutically acceptable acid addition salt thereof or an enantiomer thereof.

6. A derivative according to claim 1, which is (±)-4-{2-[4-(7-methoxy-1-naphthyl)-1-piperazinyl]ethyl}-6-methyl-3,4-dihydro-2-(1H)-quinolinone, or a pharmaceutically acceptable acid addition salt thereof or an enantiomer thereof.

7. A derivative according to claim 1, which is 4-{2-[4-(1-naphthyl)-1-piperazinyl]ethyl}-2(1H)-quinolinone or a pharmaceutically acceptable acid addition salt thereof.

8. A pharmaceutical composition which comprises a pharmaceutically effective amount of a derivative as defined in claim 1 and a pharmaceutically acceptable excipient.

* * * * *